US008858492B2

(12) United States Patent
Fitzgerald et al.

(10) Patent No.: US 8,858,492 B2
(45) Date of Patent: Oct. 14, 2014

(54) OPHTHALMIC SURGERY KITS FOR PRIMING TUBES FOR OPHTHALMIC SURGICAL PROCEDURES

(75) Inventors: Matthew J. Fitzgerald, St. Louis, MO (US); Merlin Hall, Chesterfield, MO (US); Robert Doyle, Ladue, MO (US); Michael Versemann, St. Charles, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 446 days.

(21) Appl. No.: 13/093,950

(22) Filed: Apr. 26, 2011

(65) Prior Publication Data

US 2011/0295193 A1    Dec. 1, 2011

Related U.S. Application Data

(60) Provisional application No. 61/348,429, filed on May 26, 2010.

(51) Int. Cl.
*A61F 9/007*  (2006.01)
*A61M 1/00*  (2006.01)

(52) U.S. Cl.
CPC .......... *A61F 9/00736* (2013.01); *A61M 1/0058* (2013.01); *A61M 2209/06* (2013.01)
USPC ............................................ 604/22; 604/131

(58) Field of Classification Search
USPC ................... 604/22, 118–121, 500, 131, 151
See application file for complete search history.

(56) References Cited

U.S. PATENT DOCUMENTS

| 6,302,653 | B1 | 10/2001 | Bryant et al. | 417/53 |
| 8,323,271 | B2 * | 12/2012 | Humayun et al. | 606/1 |
| 2006/0086634 | A1 * | 4/2006 | Steppe | 206/438 |
| 2007/0135752 | A1 | 6/2007 | Domash et al. | 604/19 |

FOREIGN PATENT DOCUMENTS

WO    WO 2010/047703 A2    4/2010

OTHER PUBLICATIONS

International Search Report (PCTISA/210) and Written Opinion (PCT/ISA/237) mailed on Sep. 6, 2011.

* cited by examiner

*Primary Examiner* — Kevin C Sirmons
*Assistant Examiner* — Phillip Gray
(74) *Attorney, Agent, or Firm* — Michael L. Smith (57) ABSTRACT

An ophthalmic surgery kit includes a priming vessel defining a reservoir for holding a fluid, an auxiliary aspiration channel, an irrigation channel, a handpiece channel, and an ophthalmic surgical handpiece retained by the handpiece channel. The ophthalmic surgical handpiece includes a tip disposed within the reservoir. An auxiliary aspiration tube 15 retained by the auxiliary aspiration channel with a first end disposed within the reservoir. An irrigation tube first end is retained by the irrigation channel within the reservoir.

14 Claims, 6 Drawing Sheets

OPHTHALMIC SURGERY KITS FOR PRIMING TUBES FOR OPHTHALMIC SURGICAL PROCEDURES

CROSS-REFERENCE TO RELATED APPLICATIONS

This application claims the benefit of U.S. Provisional Application No. 61/348,429, filed May 26, 2010, the entire disclosure of which is incorporated herein by reference.

BACKGROUND

1. Field

The present invention is directed to ophthalmic surgery kits. More specifically, the present disclosure is directed towards an ophthalmic surgery kit having a priming vessel, for priming at least one tube useable in an ophthalmic surgical procedure.

2. Description of the Related Art

The statements in this section merely provide background information related to the present disclosure and may not constitute prior art.

Ophthalmic surgical procedures generally employ irrigation and aspiration lines for transmitting fluid to and from a surgical site, i.e., a patient's eye. Prior to performing an ophthalmic surgical procedure, the irrigation and aspiration lines are filled with fluid to remove any air within the lines. It is common practice for a surgical assistant or other person to set-up for an ophthalmic surgical procedure by unpacking each component to be used in the ophthalmic surgical procedure, e.g., ophthalmic surgical handpieces, irrigation and aspiration tubes, etc., inserting an ophthalmic surgical handpiece and various lines in a cup or a beaker, and then separately filling the cup/beaker by the irrigation line. The set-up is time consuming for the surgical assistant, and in some instances, irrigation fluid may overflow from the cup/beaker.

Therefore, there exists the need for an improved ophthalmic surgery kit for efficient priming of an irrigation and/or aspiration tube useable in an ophthalmic surgical procedure.

BRIEF DESCRIPTION OF THE DRAWINGS

The drawings described herein are for illustration purposes only and are not intended to limit the scope of the present disclosure in any way.

DETAILED DESCRIPTION OF THE PREFERRED EMBODIMENT

The following description is merely exemplary in nature and is not intended to limit the present disclosure, application, or uses.

Figure 1:
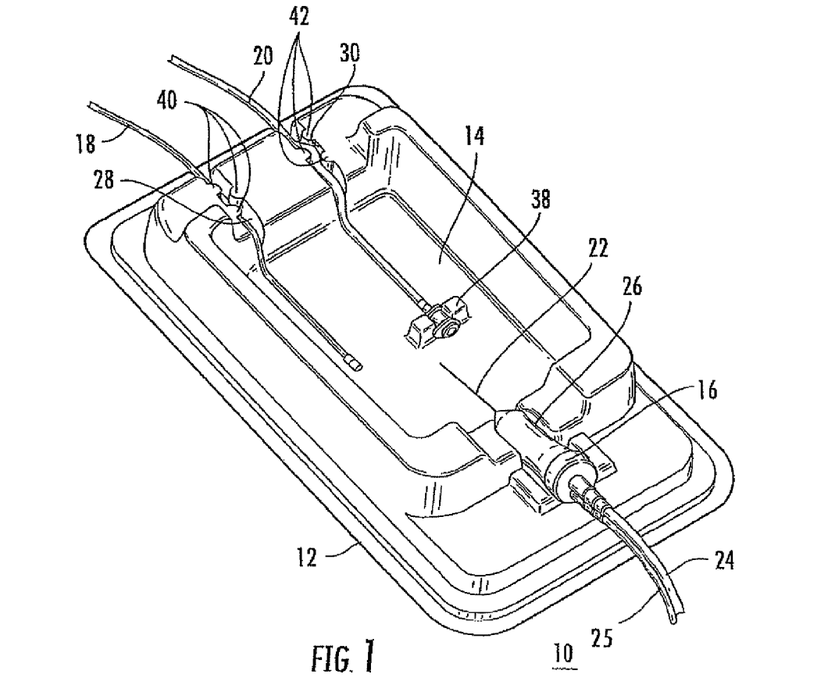
FIG. 1 is a perspective view of an ophthalmic surgery kit, according to the present disclosure.

According to one embodiment of the present disclosure, an ophthalmic surgery kit 10 is illustrated in FIG. 1. The ophthalmic surgery kit 10 includes a priming vessel 12 defining a reservoir 14 for holding fluid, an ophthalmic surgical handpiece 16, an irrigation tube 18, and an auxiliary aspiration tube 20. The ophthalmic surgical handpiece 16 includes a tip 22 for insertion into a surgical site, and an aspiration tube 24 for coupling an ophthalmic surgical console to aspirate fluid and/or tissue from the surgical site, and a pneumatic line 25 for driving handpiece 16. The ophthalmic surgical handpiece 16 is retained by a handpiece channel 26 defined by the priming vessel 12, such that the tip 22 of the ophthalmic surgical handpiece 16 is disposed within the reservoir 14. The irrigation tube 18 is retained by an irrigation channel 28, and the auxiliary aspiration tube 20 is retained by an auxiliary aspiration channel 30. The auxiliary aspiration tube 20 includes a first end disposed within the reservoir 14, and the irrigation tube 18 includes a first end disposed within the reservoir 14.

Figure 2:
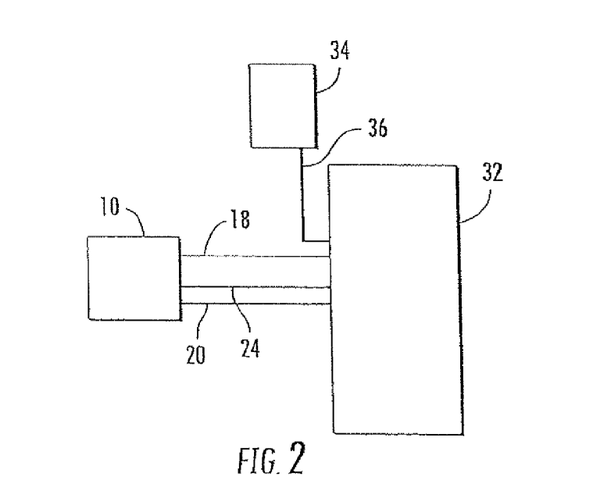
FIG. 2 is a block diagram of an ophthalmic surgery pump system, including the ophthalmic surgery kit of FIG. 1.

The ophthalmic surgery kit 10 may be pre-assembled by a manufacturer with the ophthalmic surgical handpiece 16, the irrigation tube 18, and the auxiliary aspiration tube 20 retained by the priming vessel 12. In use, a user, e.g., surgical assistant, nurse, surgeon, etc., removes the pre-assembled ophthalmic surgery kit 10 from a sterile package (not shown). As illustrated in FIG. 2, the user couples the aspiration tube 24 and the auxiliary aspiration tube 20 to an ophthalmic surgical console 32 (typically the connection to console 32 is made via a cassette, not shown). The user also couples the irrigation tube 18 to an irrigation source 34 via an unshown cassette inserted into console 32 (also typically via a cassette). As shown, the irrigation source 34 is coupled to the irrigation tube 18 through an irrigation supply tube 36 coupled to the ophthalmic surgical console 32. It should be appreciated that an irrigation tube and an irrigation source may be coupled differently, directly, or indirectly in other embodiments, to provide fluid flow through the irrigation tube to a reservoir.

Once the aspiration and irrigation tubes 18, 20, and 24 are coupled as shown, the user initiates a priming sequence. According to the priming sequence, the ophthalmic surgical console 32, through one or more plungers adjacent to the irrigation tube 18 and/or irrigation supply tube 36, controls the dispensing of a pre-determined volume of fluid, e.g., 75 milliliters, etc., into the reservoir 14 through the irrigation tube 18, thereby priming the irrigation tube 18. In addition, console 32 will open fluid vent lines to push irrigation fluid through aspiration tubes 20, 24, and handpiece 16 until each is fully primed. To efficiently accomplish this, irrigation source 34 can be raised to create added pressure or irrigation source 34 can be pressurized, as is known. As a result, the tip 22 of the ophthalmic surgical handpiece 16, and the first end of the auxiliary aspiration tube 20 are immersed in fluid, e.g., balanced salt solution ("BSS"), etc. Subsequently or simultaneously, a portion of the pre-determined volume of fluid may be evacuated through the aspiration tube 24, the auxiliary aspiration tube 20, or handpiece 16 through negative pressure supplied by the ophthalmic surgical console 32. Accordingly, the pushing of fluid or the aspiration of fluid may prime the aspiration tube 24, the auxiliary aspiration tube 20, and/or the handpiece 16. Once the priming sequence is completed, each of the ophthalmic surgical handpiece 16, the irrigation tube 18, and the auxiliary aspiration tube 20 are primed, i.e., substantially free of air bubbles, and ready to be used in an ophthalmic surgical procedure. Pre-assembly of the ophthalmic surgery kit 10 eliminates set-up time and provides efficiencies prior to an ophthalmic surgical procedure. Conveniently, reservoir 14 now provides a source of fluid to prime additional surgical instruments and associated tubing that may be needed.

Moreover, the ophthalmic surgical console 32 automatically controls, based on the priming sequence, fluid flow to/from the reservoir 14 for priming a plurality of tubes and surgical handpieces. In this manner, user participation in the priming sequence, after set-up, may be limited to providing one or more inputs to the ophthalmic surgical console 32, while eliminating overflow conditions. It should be appreciated that in other embodiments, a different level of user interaction may be required. In one example, a user may simply indicate a type of ophthalmic surgical procedure and/or ophthalmic surgical handpiece, while in another example, a user may input a pre-determined volume of fluid to an ophthalmic surgical console. In other embodiments, a level of automation of a priming sequence may be different depending on at least the type of ophthalmic surgical procedure, an ophthalmic surgical handpiece, a surgical protocol, and/or one or more preferences of a user, etc. Generally, when the aspiration tubes 20, 24 are primed, the ophthalmic surgical console 32 provides a visible and/or audible signal to the user.

As shown, the aspiration tube 24 and the auxiliary aspiration tube 20 extend from the priming vessel 12. It should be appreciated that in other embodiments, a different number of aspiration tubes may be employed. For example, only one aspiration tube incorporated in an ophthalmic surgical handpiece may extend from a priming vessel in at least one embodiment of the present disclosure. Further, the number of irrigation tubes retained by a priming vessel may also be different in other embodiments of the present disclosure. The number of aspiration and/or irrigation tubes included in an ophthalmic surgery kit may, for example, be based on the type of an ophthalmic surgical procedure, an ophthalmic surgical console, an ophthalmic surgical handpiece, commonality of an ophthalmic surgery kit, other factors, and/or various combinations thereof, etc.

Figure 3:
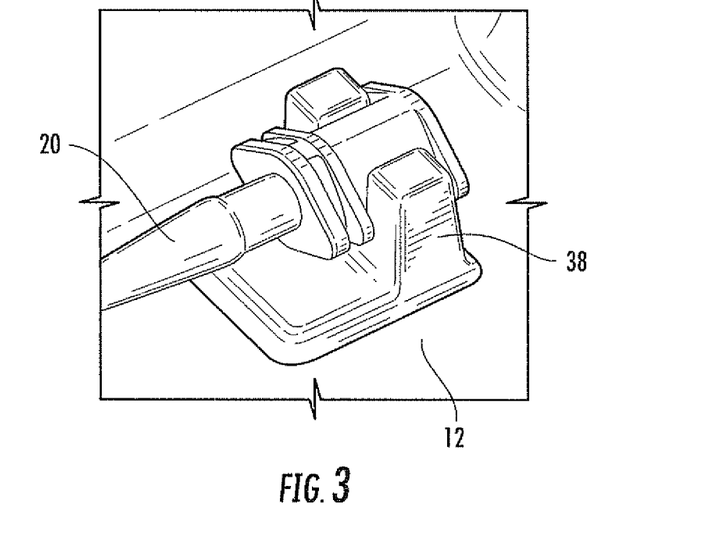
FIG. 3 is a partial perspective view of the auxiliary aspiration tube included in the ophthalmic surgery kit of FIG. 1.

Referring again to FIG. 1, the first end of the auxiliary aspiration tube 20 is releasably coupled by an aspiration clamp 38. A detailed view of the aspiration clamp 38 is illustrated in FIG. 3. The aspiration clamp 38 is disposed within the reservoir on a lower surface of the priming vessel 12. The aspiration clamp 38 may form a snap or friction fit with the auxiliary aspiration tube 20, such that when fluid is held in the reservoir 14, the first end of the auxiliary aspiration tube 20 is retained and immersed in fluid. After the auxiliary aspiration tube 20 is primed, the auxiliary aspiration tube 20 may be removed from the aspiration clamp 38 and coupled to an ophthalmic surgical handpiece or other suitable instrument for use in an ophthalmic surgical procedure. In this particular embodiment, the aspiration clamp 38 is molded with the priming vessel 12. It should be appreciated that in other embodiments of the present disclosure, a different type of clamp or other suitable member may be coupled to, connected to, molded with, formed with, or fastened to a priming vessel to releasably couple an auxiliary aspiration tube for immersion in fluid.

Figure 4:
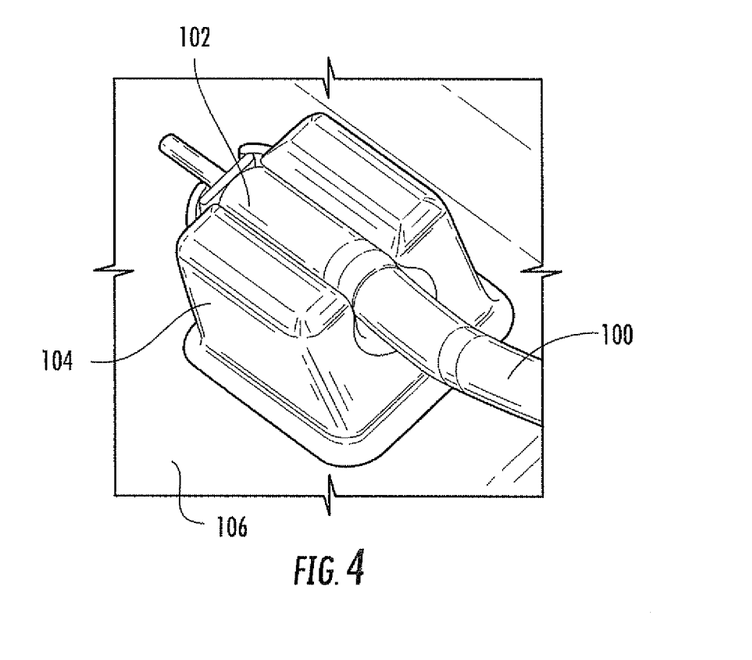
FIG. 4 is a partial perspective view of an irrigation tubing, including an infusion cannula according to an embodiment of the present disclosure.

Further, the first end of the irrigation tube 18 is provided to dispense fluid into the reservoir 14, but is not coupled to any surface of the reservoir 14, i.e., free-floating. Alternatively in various embodiments of the present disclosure, an end of an irrigation tube may be fixedly or releasably coupled to a priming vessel to ensure fluid is dispensed efficiently into a reservoir defined by the priming vessel. In one example embodiment illustrated in FIG. 4, an irrigation tube 100 includes an infusion cannula 102 at an end disposed within a reservoir. As shown, the infusion cannula 102 may be retained by an irrigation clamp 104, positioned in a bottom surface of a reservoir defined by a priming vessel 106. The irrigation clamp 104 may be molded with the priming vessel 106. It should be appreciated that various other types of members for coupling an irrigation tube and/or an infusion cannula may be employed in other embodiments. One or more of these types of members may be coupled to, connected to, molded with, formed with, or fastened to a priming vessel.

Referring again to FIG. 1, the priming vessel 12 includes three protuberances 40 extending into the irrigation channel 28. The protuberances 40 contacts the irrigation tube 18 at least during insertion, providing a snap or friction fit, and generally inhibits dislodgement of the irrigation tube 18 during shipment, set-up, and/or a priming sequence of the ophthalmic surgery kit 10. Similarly, the priming vessel 12 includes three protuberances 42 extending into the auxiliary aspiration channel 30, for inhibiting removal of the auxiliary aspiration tube 20 from the auxiliary aspiration channel 30. It should be appreciated that a different type, number, and/or size of protuberances may be employed in other embodiments of the present disclosure. Further, different mechanical features may be defined by a priming vessel or coupled to the priming vessel to releasably retain an irrigation and/or aspiration tube to the priming vessel, and/or within a channel defined by the priming vessel. Further still, a shape and/or size of a channel may be configured to retain a tube disposed therein.

While the priming vessel 12 illustrated in FIG. 1 is generally rectangular shaped, it should be appreciated that a different shape of priming vessel, e.g., circular, triangular, polygonal, etc., may be employed in other embodiments of the present disclosure. Further, a shape of a reservoir defined by a priming vessel may be different from a shape of the priming vessel. Also, the priming vessel 12 includes vacuum formed thermoplastic. Other suitable materials and/or methods of making a priming vessel, well known in the art, should be considered within the spirit of the present disclosure.

Figure 5:
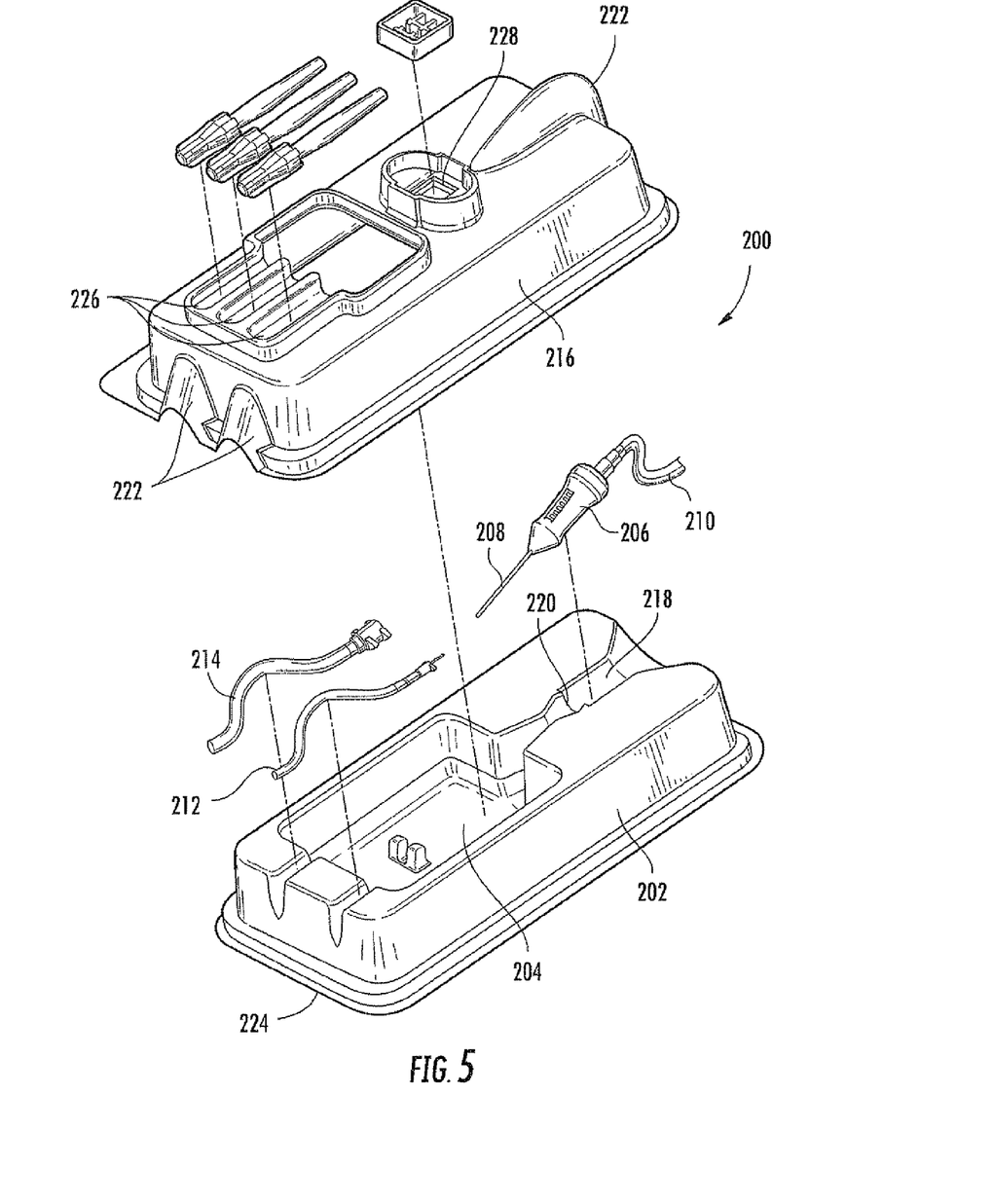
FIG. 5 is an exploded view of an ophthalmic surgery kit, according to the present disclosure.

FIG. 5 illustrates an exploded view of an ophthalmic surgery kit 200, according to another embodiment of the present disclosure. The ophthalmic surgery kit 200 includes a priming vessel 202 defining a reservoir 204, a vitreous cutter 206 having a tip 208, an aspiration tube 210, an irrigation tube 212 for coupling to an irrigation source, and an auxiliary aspiration tube 214. The aspiration tubes 210, 214 extend beyond the ophthalmic surgery kit 200 to couple to an ophthalmic surgical console, and the irrigation tube extends beyond the ophthalmic surgery kit 200 to couple to an irrigation source, directly or indirectly. It should be appreciated that in various other embodiments, different types, sizes, and/or shapes of ophthalmic surgical handpieces may be included in an ophthalmic surgery kit. For example, a phacoemulsification handpiece or a channel for retaining a phaco handpiece on vessel 202 may be included in an ophthalmic surgery kit.

The ophthalmic surgery kit 200 further includes a cover 216. The cover 216 defines a shape generally complimentary to the priming vessel 202, such that the cover 216 fits over at least a portion of the priming vessel 202, and forms a friction fit therewith. The cover 216 generally encloses the reservoir 204. When assembled, the cover 216 is disposed to protect the vitreous cutter 206, the irrigation tube 212, and the auxiliary aspiration tube 214 during shipment, set-up, and/or a priming sequence. The cover 216 may be removed to provide access to the vitreous cutter 206, the irrigation tube 212, and the auxiliary aspiration tube 214. It should be appreciated that different sizes and/or shapes of covers may be included in other embodiments. In at least one embodiment, a cover may be hingedly coupled to a priming vessel. Further, in at least one embodiment, a cover may be omitted.

Figure 6:
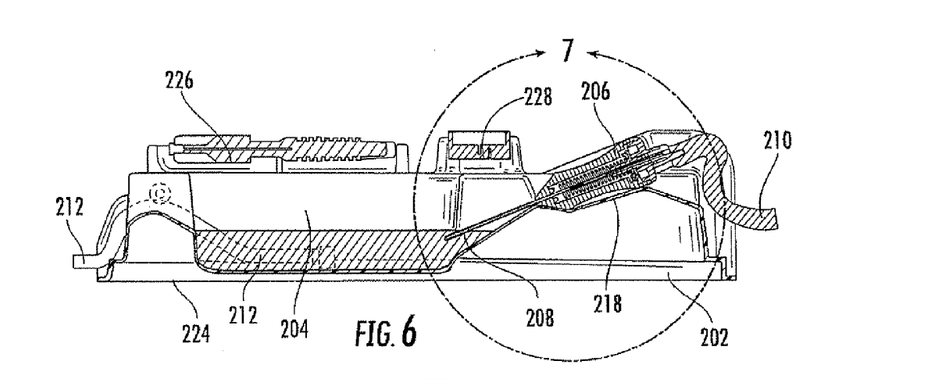
FIG. 6 is a cross-sectional view of the ophthalmic surgery kit of FIG. 4.

FIG. 6 illustrates a cross-sectional view of the assembled ophthalmic surgery kit 200. The priming vessel 202, defines a handpiece channel 218 for retaining the vitreous cutter 206. The handpiece channel 218 includes a part of a conical shape, which in combination with a rib 220 (best seen in FIG. 5), provides snap retention of the vitreous cutter 206, and prevents the vitreous cutter 206 from sliding into the reservoir 204. The handpiece channel 218 further permits user access to the vitreous cutter 206 for removal during an ophthalmic surgical procedure.

Figure 7:
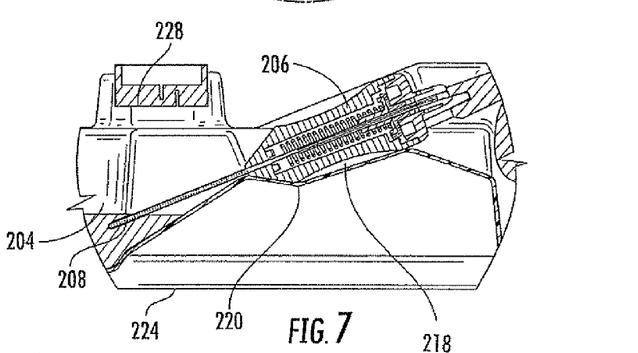
FIG. 7 is a partial cross-sectional view, as indicated in FIG. 5.

As shown in FIG. 7, the tip 208 of the vitreous cutter 206 is disposed within the reservoir 204. The shape of the handpiece channel 218 inhibits the vitreous cutter 206 from contacting a bottom surface of the priming vessel, potentially preventing damage to the tip 208 of the vitreous cutter 206, and/or the priming vessel 202. After the vitreous cutter 206 is removed from the handpiece channel 218 of the priming vessel 202, it may be returned one or more times during an ophthalmic surgical procedure. In other embodiments, a handpiece channel may define a different shape and/or size complimentary to or different from a shape/size of an ophthalmic surgical handpiece retained therein. The shape and/or size of the handpiece channel may be dependent on aspects of the intended retention, insertion, and/or removal of the ophthalmic surgical handpiece.

As shown in FIG. 5, the cover 216 includes a number of bulges 222 to accommodate the vitreous cutter 206, the irrigation tube 212, and the auxiliary aspiration tube 214 in the priming vessel 202, when the cover 216 is disposed over the priming vessel 202. The bulges 222 defined by the cover 216, permit the irrigation and aspiration tubes 210, 212, and 214 to extend from ophthalmic surgery kit 200. Cover 216 may be supported by bottom surface 224. Further as shown, the bulge 222 over the vitreous cutter 206 defines a shape complimentary to the part of the conical shape defined by the priming vessel 202, thereby aiding in retention of the vitreous cutter 206 while disposed over the priming vessel 202. It should be appreciated that a different number, shape, and/or configuration of bulges may be employed in other embodiments to ensure accommodation of various tubes and/or ophthalmic surgical handpieces.

As explained above, the ophthalmic surgery kit 200 is generally received by the user pre-assembled. The cover 216 may be molded to retain additional components external to the reservoir 204, as generally shown in FIG. 5. For example, the cover 216 defines trocar retention slots 226 and a pin block retention slot 228. The trocar retention slots 226 permit up to three trocars to be retained by the cover 216 for convenient access. Similarly, the pin block retention slot 228 provides for retention of a pin block for convenient access to entry site alignment devices, as indicated above. It should be appreciated that different components used prior to, during, and/or after an ophthalmic surgical procedure may be conveniently retained by a cover and/or a priming vessel in other embodiments of the present disclosure.

Figure 8:
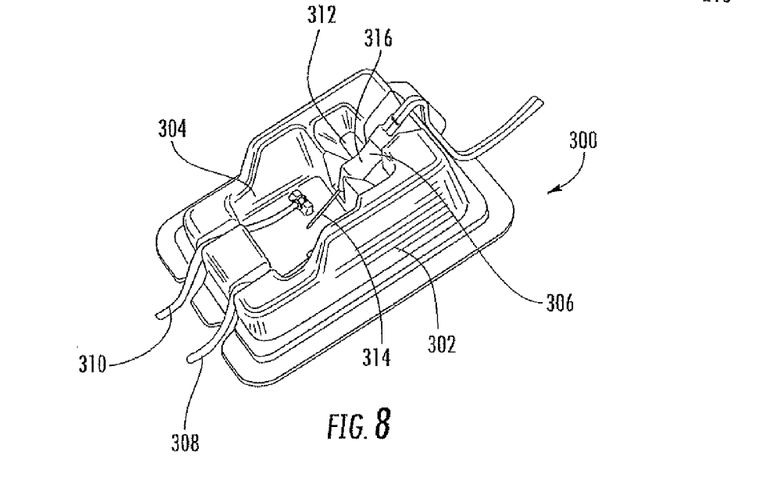
FIG. 8 is a perspective view of an ophthalmic surgery kit, according to the present disclosure.
Figure 9:
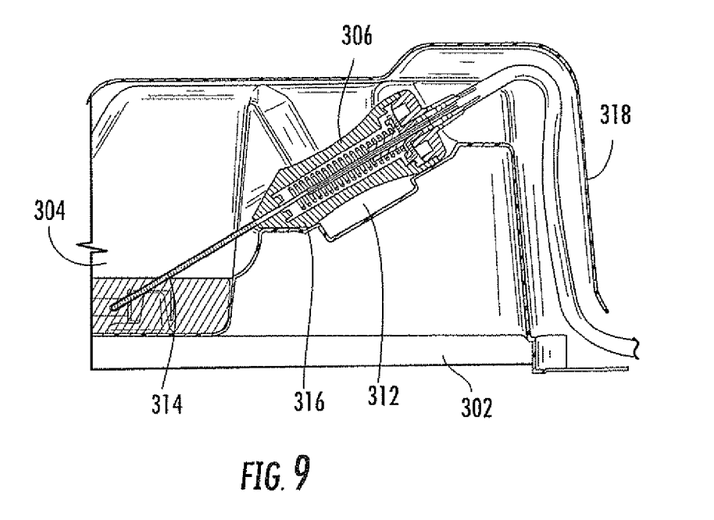
FIG. 9 is a partial cross-sectional view of an ophthalmic surgical handpiece included in the ophthalmic surgery kit of FIG. 7.

According to another embodiment of the present disclosure, an ophthalmic surgery kit 300 is illustrated in FIG. 8. The ophthalmic surgery kit 300 includes a priming vessel 302 defining a reservoir 304, and an ophthalmic surgical handpiece 306. As shown, the priming vessel 302 includes an increased height for retention of the ophthalmic surgical handpiece 306, and a decreased height, compared to the embodiment of FIGS. 1-7, for retention of an irrigation tube 308 and an auxiliary aspiration tube 310. The increased height, e.g., 2 inches, 2⅛ inches, etc., permits a handpiece channel 312 defined by the priming vessel 302, to retain the ophthalmic surgical handpiece 306 at an angle of about 45 degrees, as shown in FIG. 9. A sufficient angle permits the ophthalmic surgical handpiece 306 to be disposed with its tip 314 disposed in the reservoir, while limiting potential contact between fluid in the reservoir 304 and the body 316 of the ophthalmic surgical handpiece 306. It should be appreciated that a priming vessel and/or a handpiece channel may include a different height, size, shape, and/or configuration to retain an ophthalmic surgical handpiece at a different angle to affect user access to the ophthalmic surgical handpiece, enable efficient priming of tubes in fluidic communication therewith, and/or protection of the ophthalmic surgical handpiece, e.g., a needle coupled to the ophthalmic surgical handpiece, etc. FIG. 9 illustrates a partial cross-section of the ophthalmic surgery kit 300 including a cover 318.

In the embodiments of FIG. 8, the ophthalmic surgical handpiece 306 may be removed upward, as opposed to in parallel with the longitudinal axis of the handpiece channel 312, which may be preferred by one or more users. It should be appreciated that a size, shape, and/or dimension of a priming vessel may be different to alter access to an ophthalmic surgical handpiece in other embodiments of the present disclosure.

Additionally, the reservoir 304 is configured to retain a volume of BSS, generally in excess of a pre-determined volume defined by a priming sequence. A capacity of a reservoir defined by a priming vessel may be different, e.g., by varying the size and/or shape, etc., for various embodiments of the present disclosure. The capacity is generally selected to hold sufficient fluid to prime each of the aspiration tubes disposed within the reservoir, e.g., 75 milliliters, etc. It should also be understood that the size and/or shape of the priming vessel may also be different to provide a different volume of fluid to, for example, affect fluid flow within tubes disposed therein.

Figure 10:
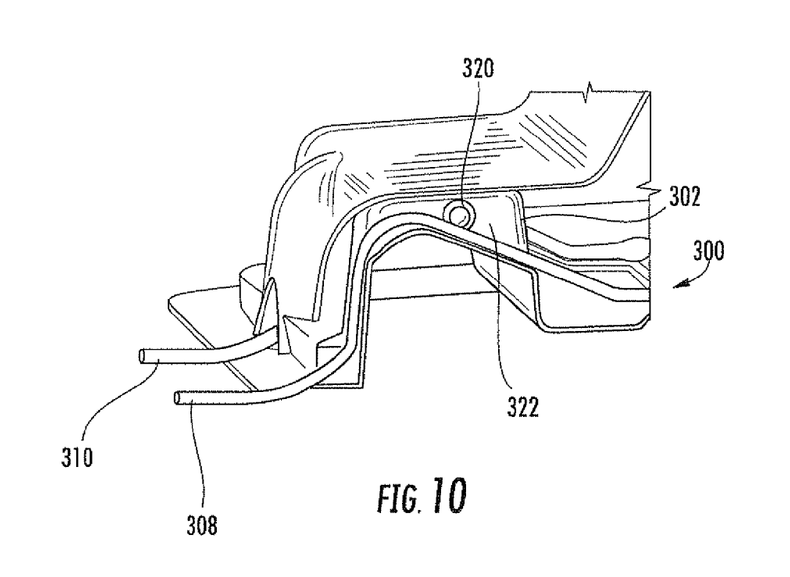
FIG. 10 is a partial perspective cross-sectional view of an irrigation tube included in the ophthalmic surgery kit of FIG. 7.
Figure 11:
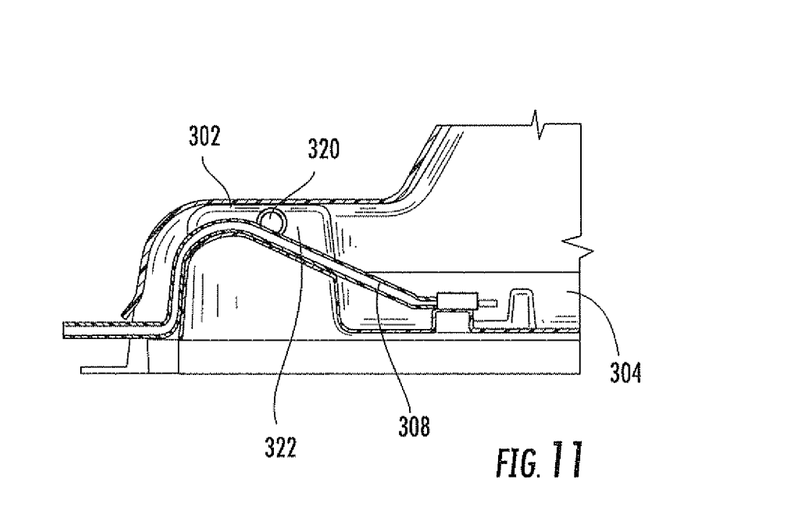
FIG. 11 is a partial cross-sectional side view of the irrigation tube included in the ophthalmic surgery kit of FIG. 7.
Figure 12:
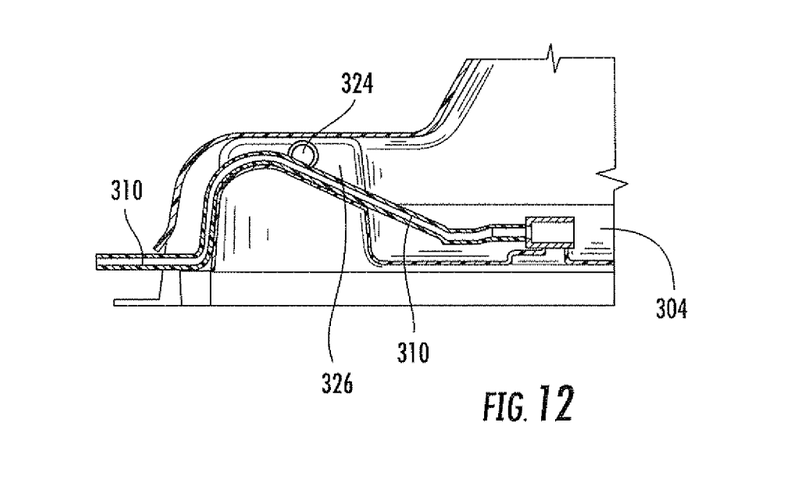
FIG. 12 is a partial cross-sectional side view of an auxiliary aspiration tube included in the ophthalmic surgery kit of FIG. 7.

FIGS. 10-11 provide detailed views of a protuberance 320 included in the priming vessel 302 and extending into an irrigation channel 322 for retaining the irrigation tube 308. Similarly, as shown in FIG. 12, a protuberance 324 included in the priming vessel extends into an auxiliary aspiration channel 326 for retaining the auxiliary aspiration tube 310. It should be appreciated that a different type, size, number, and/or shape of protuberances may be employed in other embodiments of the present disclosure. Additionally or alternatively, a cover disposed over a priming vessel may include one or more projections, fasteners, etc. to inhibit removal of an irrigation and/or aspiration tube from a priming vessel during shipment and/or a priming sequence.

Although several aspects of the present disclosure have been described above with reference to ophthalmic surgery kits, it should be understood that various aspects of the present disclosure are not limited to ophthalmic surgery kits, and can be applied to a variety of other ophthalmic surgical systems, devices, and methods.

By implementing any or all of the teachings described above, a number of benefits and advantages can be attained, including improved reliability, reduced down time, elimination or reduction of redundant components or systems, avoiding unnecessary or premature replacement of components or systems, and a reduction in overall system and operating costs.

We claim:

1. An ophthalmic surgery system comprising:
   an ophthalmic surgical console; and
   an ophthalmic surgery kit for use with the surgical console, including:
   a priming vessel defining a reservoir for holding a fluid, an auxiliary aspiration channel, an irrigation channel, and a handpiece channel;
   an ophthalmic surgical handpiece retained by the handpiece channel, the ophthalmic surgical handpiece, including a tip for insertion into a surgical site, and an aspiration tube coupled to the ophthalmic surgical console and transmitting fluid and tissue from the surgical site, the tip being disposed within the reservoir;
   an auxiliary aspiration tube retained by the auxiliary aspiration channel and having a first end disposed within the reservoir, the auxiliary aspiration tube having a second end coupled to the ophthalmic surgical console;
   an irrigation tube coupled to the ophthalmic surgical console and retained by the irrigation channel and having a first end disposed within the reservoir for dispensing fluid into the reservoir; and
   wherein the tip and the first end of the auxiliary aspiration tube becomes immersed in the fluid when a pre-determined volume of fluid, defined by a priming sequence controlled by the ophthalmic surgical console, is dispensed by each of the irrigation tube, the aspiration tube, the surgical handpiece, and the auxiliary aspiration tube into the reservoir, such that fluid flow controlled by the ophthalmic surgical console primes the surgical handpiece, the irrigation tube, the aspiration tube, and the auxiliary aspiration tube.

2. The ophthalmic surgery kit of claim 1, wherein the priming vessel includes at least one protuberance extending into the auxiliary aspiration channel for inhibiting removal of the auxiliary aspiration tube from the auxiliary aspiration channel.

3. The ophthalmic surgery kit of claim 2, wherein the priming vessel includes at least one protuberance extending into the irrigation channel for inhibiting removal of the irrigation tube from the irrigation channel.

4. The ophthalmic surgery kit of claim 1, wherein each of the auxiliary aspiration channel and the irrigation channel are integrally formed with the priming vessel.

5. The ophthalmic surgery kit of claim 1, wherein priming vessel includes an aspiration clamp disposed at least partially within the reservoir, the first end of the auxiliary aspiration tube being releasably coupled by the aspiration clamp.

6. The ophthalmic surgery kit of claim 5, wherein the irrigation tube includes an infusion cannula releasably coupled by an irrigation clamp disposed at least partially within the reservoir.

7. The ophthalmic surgery kit of claim 1, further comprising a cover disposed over the priming vessel, thereby enclosing the reservoir.

8. The ophthalmic surgery kit of claim 7, wherein the cover defining a bulge configured to permit said aspiration tube to extend from the priming vessel when the cover is coupled to the priming vessel.

9. The ophthalmic surgery kit of claim 1, wherein the handpiece channel defines at least a portion of a conical shape, including a snap feature for releasably coupling the ophthalmic surgical handpiece.

10. The ophthalmic surgery kit of claim 1, wherein the ophthalmic surgical handpiece includes a vitreous cutter.

11. A method of priming a plurality of tubes and surgical handpieces prior to an ophthalmic surgical procedure, the method comprising:
    providing a pre-assembled ophthalmic surgery kit, the pre-assembled ophthalmic surgery kit, including an irrigation tube, an ophthalmic surgical handpiece having a tip, and an aspiration tube, and a priming vessel defining a reservoir, an irrigation channel retaining the irrigation tube, and a handpiece channel retaining the ophthalmic surgical handpiece, said tip and a first end of the irrigation tube being disposed within the reservoir;
    coupling a first end of the aspiration tube to an ophthalmic surgery pump system;
    coupling a second end of the irrigation tube to an irrigation source for dispensing fluid into the reservoir; and
    initiating a priming sequence to push a pre-determined volume of fluid into the reservoir through the irrigation tube, the aspiration tube, and the surgical handpiece until the irrigation tube, the aspiration tube, and the surgical handpiece are primed.

12. The method of claim 11, wherein the pre-assembled ophthalmic surgery kit includes a cover disposed over the priming vessel; and
    further comprising removing the cover disposed over the priming vessel to access the ophthalmic surgical handpiece prior to an ophthalmic surgical procedure.

13. The method of claim 11, wherein the pre-assembled ophthalmic surgery kit includes an auxiliary aspiration tube retained by an auxiliary aspiration channel defined by the priming vessel; the auxiliary aspiration tube including a first end disposed within the reservoir; and a portion of the pre-determined volume of fluid being evacuated through the auxiliary aspiration tube.

14. The method of claim 13, further comprising coupling the first end of the auxiliary aspiration tube to a second ophthalmic surgical handpiece.

* * * * *